US010360681B2

(12) United States Patent
Humbert

(10) Patent No.: US 10,360,681 B2
(45) Date of Patent: Jul. 23, 2019

(54) METHOD, A SYSTEM AND A COMPUTER PROGRAM FOR DETERMINING DATA DEFINING AN ESTIMATE OF THE THICKNESS AND DENSITY OF A CORTICAL BONE TISSUE STRUCTURE OF INTEREST FROM IMAGING DATA

(71) Applicant: GALGO MEDICAL, S.L., Barcelona (ES)

(72) Inventor: Ludovic Humbert, Barcelona (ES)

(73) Assignee: GALGO MEDICAL, S.L., Barcelona (ES)

( * ) Notice: Subject to any disclaimer, the term of this patent is extended or adjusted under 35 U.S.C. 154(b) by 77 days.

(21) Appl. No.: 15/577,597

(22) PCT Filed: May 30, 2016

(86) PCT No.: PCT/EP2016/062133
§ 371 (c)(1),
(2) Date: Nov. 28, 2017

(87) PCT Pub. No.: WO2016/189166
PCT Pub. Date: Dec. 1, 2016

(65) Prior Publication Data
US 2018/0144473 A1 May 24, 2018

(30) Foreign Application Priority Data
May 28, 2015 (EP) .................................... 15382280

(51) Int. Cl.
*G06K 9/00* (2006.01)
*G06T 7/00* (2017.01)
(Continued)

(52) U.S. Cl.
CPC ............ *G06T 7/0014* (2013.01); *A61B 6/032* (2013.01); *A61B 6/505* (2013.01); *A61B 6/5217* (2013.01);
(Continued)

(58) Field of Classification Search
CPC .......................................... G06T 2207/10081
See application file for complete search history.

(56) References Cited

U.S. PATENT DOCUMENTS

2012/0224758 A1    9/2012   Treece et al.
2012/0232375 A1    9/2012   Zebaze et al.
(Continued)

FOREIGN PATENT DOCUMENTS

WO    WO2011042738    4/2011

OTHER PUBLICATIONS

Celenk et al (NPL "Bone Density Measurement Using Computed Tomography", ISBN 978-953-307-378-1, p. 16, Jan. 2012.) (Year: 2012).*

(Continued)

*Primary Examiner* — Oneal R Mistry
(74) *Attorney, Agent, or Firm* — Jenkins, Wilson, Taylor & Hunt, P.A.

(57) ABSTRACT

Provided are methods for determining data defining an estimate of the thickness and density of a cortical bone tissue structure of interest from imaging data. The methods can include modelling measured variations of an imaging parameter along a line crossing a cortical bone tissue structure of interest as a function having a thickness parameter, a first density parameter, and a blur parameter; determining a thickness-density relationship between bone tissue structure density and bone tissue structure thickness from multiple thickness and density measurements made on a reference cortical bone tissue structure of a subject which is not (Continued)

the patient; and fitting the function to the measured variations while ensuring the first density parameter and thickness parameter follow the thickness-density relationship, to search for optimal values that include data defining an estimate of the thickness and density of the cortical bone tissue structure of interest. Also provided are systems and computer programs to implement the disclosed methods.

19 Claims, 7 Drawing Sheets

(51) Int. Cl.
    *A61B 6/00* (2006.01)
    *A61B 6/03* (2006.01)
    *G01N 23/04* (2018.01)

(52) U.S. Cl.
    CPC .......... *G06T 7/0012* (2013.01); *A61B 6/5247* (2013.01); *A61B 6/582* (2013.01); *G01N 23/04* (2013.01); *G06T 2207/10081* (2013.01); *G06T 2207/20168* (2013.01); *G06T 2207/30008* (2013.01)

(56) References Cited

U.S. PATENT DOCUMENTS

| | | | |
|---|---|---|---|
| 2015/0250552 A1* | 9/2015 | Radermacher | A61F 2/46 703/11 |
| 2016/0262686 A1* | 9/2016 | Tsuji | A61B 6/501 |
| 2018/0110459 A1* | 4/2018 | Nevo | A61B 5/055 |

OTHER PUBLICATIONS

Bousson et al. (2006) Volumetric quantitative computed tomography of the proximal femur: relationships linking geometric and densitometric variables to bone strength. Role for compact bone. Osteoporos Int. 17:855-864.

El Maghraoui et al. (2008) DXA scanning in clinical practice. QJM 101:605-617.

International Search Report corresponding to International Application No. PCT/EP2016/062133 dated Sep. 9, 2016.

Johnell et al. (2006) An estimate of the worldwide prevalence and disability associated with osteoporotic fractures. Osteoporos Int. 17:1726-1733.

Moré, J. (1978) The Levenberg-Marquardt Algorithm: Implementation and Theory. Numerical Analysis. 630:105-116. Edited by G.A. Watson (Springer Berlin Heidelberg.

Pakdel et al. (2012) Generalized method for computation of true thickness and x-ray intensity information in highly blurred submillimeter bone features in clinical CT images. Physics in Medicine and Biology 57:8099-8116.

Prevrhal et al. (1999) Accuracy limits for the determination of cortical width and density: the influence of object size and CT imaging parameters. Physics in medicine and biology 44:751-764.

Streekstra et al. (2007) Model-based cartilage thickness measurement in the submillimeter range. Medical Physics 34:3562-3570.

Treese et al. (2010) High resolution cortical bone thickness measurement from clinical CT data. Med. Image Anal. 14:276-290.

Treece et al. (2012) Imaging the femoral cortex: thickness, density and mass from clinical CT. Med. Image Anal. 16:952-965.

Treece et al. (2015) Independant measurement of femoral cortical thickness and cortical bone density using clinical CT. Med Image Anal. 20:249-264.

Whitemarsh et al. (2011) Reconstructing the 3D Shape and Bone Mineral Density Distribution of the Proximal Femur from Dual-energy X-ray Absorptiometry. IEEE Trans Med Imaging.

* cited by examiner

METHOD, A SYSTEM AND A COMPUTER PROGRAM FOR DETERMINING DATA DEFINING AN ESTIMATE OF THE THICKNESS AND DENSITY OF A CORTICAL BONE TISSUE STRUCTURE OF INTEREST FROM IMAGING DATA

CROSS REFERENCE TO RELATED APPLICATIONS

This application is a United States National Stage entry under 35 U.S.C. § 371 of PCT International Application Serial No. PCT/EP2016/062133, filed May 30, 2016, which claims the benefit of European Patent Application Serial No. 15382280.4, filed May 28, 2015, each of which is incorporated by reference herein in its entirety.

TECHNICAL FIELD

The present invention generally concerns, in a first aspect, to a method for determining data defining an estimate of the thickness and density of a cortical bone tissue structure of interest from imaging data, and more particularly to a method allowing to determine said data defining said estimate of said thickness and density even when only regions of thin cortical bone tissue structure are present in the imaging data.

Second and third aspect of the invention respectively concern to a system and a computer program implementing the method of the first aspect.

BACKGROUND

For the year 2000, there were an estimated 9 million new osteoporotic fractures, of which 1.6 million were at the hip, 1.7 million were at the forearm and 1.4 million were clinical vertebral fractures [1]. In clinical routine, osteoporosis diagnosis is largely based on the analysis of planar images obtained by Dual-energy X-ray Absorptiometry [2]. However, direct measurements performed using DXA projections are not able to accurately quantify the bone strength and predict an individual's risk of fracture. In particular, the cortical bone anatomical distribution is a critical component in determining the resistance of a bone to fracture [3] and cannot be evaluated using direct measurements in the 2D DXA projection. Physicians have to rely on 3D imaging techniques, such as Computed Tomography (CT), Quantitative Computed Tomography (QCT) or Magnetic Resonance Imaging (MRI). QCT uses a standard X-rays CT scanner together with a calibration phantom to convert Hounsfield Units of the CT images to Bone Mineral Density (BMD) values. Those techniques generate a set of slices containing information about the cortical bone. To overcome some of the limitations associated with CT, QCT or MRI devices (radiation dose and/or low availability for osteoporosis diagnosis in clinical environment), methods were recently proposed to reconstruct in 3D bony structures from 2D DXA projections [4, 5]. Similar to CT, QCT and MRI, the reconstructed 3D volume contains information about the cortical bone.

Measuring the cortical bone thickness and density from such 3D volumes or slices is not trivial. The cortical layer can be relatively thin in comparison with the image resolution, and previous studies have shown that straightforward measurement techniques of the cortical thickness and density such as the full-width half-maximum (FWHM) method [6] become inaccurate when measuring cortical thicknesses below around 3 mm. Many anatomical regions of interest for fracture risk assessment (femoral head, femoral neck, greater trochanter or vertebral body) exhibits cortical thicknesses below 3 mm.

Model-based estimation methods for measuring the cortex are capable of superior accuracy. Pakdel et al [7] performed the fitting of a function of the cortical thickness and density, image blur and surrounding tissue densities to actual CT data. However, this inverse problem is ill-posed, and several studies demonstrated that parameters of the function should be constrained to guarantee accurate results. Steekstra et al [8] proposed to study the point spread function of the CT device to constrain the image blur. This process requires a phantom to be scanned, which would modify current clinical routine practices. Treece et al [9, 10, 13] proposed to hold the parameter determining the cortical density at a constraining value during the fitting process. Assuming the cortical density to be constant is however not realistic, as several studies observed a trend for cortical density to increase with thickness. In later work, Treece et al [11] accounted for this trend by modelling the cortical density as a piecewise function of the thickness. Searching for the optimal value for constraining the cortical density [9, 10, 13] or the optimal parameters of the thickness-density piecewise function [11] require a region of thick cortex (above around 3 mm) to be present in the CT-scans. This is however not always the case, for example if only the upper part of the proximal femur (femoral head, neck and greater trochanter) is scanned. In addition, those algorithms require additional calculation steps to obtain an accurate estimation of the constraining density value or the thickness-density piecewise function, which complicated the overall process. Incorporating a constraining density value [10] requires to perform twice the fitting of a function at each node of the surface of the bone, while the algorithm relying on the thickness-density piecewise function [11] requires five iterations. There is therefore a need for improved techniques for estimating the cortical thickness and density, in particular when only regions of thin cortex are present in the medical images.

SUMMARY

It is necessary to provide an alternative to the state of the art that covers the gaps found therein, particularly those existing when only regions of thin cortex are present in the medical images.

To that end, the present invention relates, in a first aspect, to a method for determining data defining an estimate of the thickness and density of a cortical bone tissue structure of interest from imaging data, the method comprising:

providing measured variations of an imaging parameter of imaging data defining at least one representation of a region of bone tissue of a patient including said cortical bone tissue structure of interest, said variations being measured along a line crossing said cortical bone tissue structure of interest (preferably in a substantially normal direction to a cross-section thereof) and being representative of variations of bone tissue structure density;

modelling said variations of said imaging parameter along said line as a function having at least one parameter defining said thickness of said cortical bone tissue structure of interest along said line, at least a first density parameter defining said density of said cortical bone tissue structure of interest along said line and at least one parameter representing the blur of said imaging data;

determining a thickness-density relationship between cortical bone tissue structure density and cortical bone tissue structure thickness; and fitting said function to said measured variations of said imaging parameter;

wherein said fitting comprises searching for optimal values for said at least one parameter representing the blur of the said imaging data, for said at least one parameter defining said thickness of said cortical bone tissue structure of interest and for said at least first density parameter defining said density of said cortical bone tissue structure of interest, while ensuring said at least first density parameter and said at least one parameter defining said thickness to substantially follow said thickness-density relationship;

wherein said optimal values for said at least one parameter defining said thickness of said cortical bone tissue structure of interest and for said at least first density parameter comprise, respectively, data defining said estimate of said thickness and data defining said estimate of said density of the cortical bone tissue structure of interest.

Contrary to the method disclosed by Treece et al. [11], where the mentioned thickness-density relationship was determined from measures made on the same patient, the method of the first aspect of the present invention comprises determining said thickness-density relationship from multiple thickness and density measurements made on reference imaging data of a reference cortical bone tissue structure of a subject which is not said patient, wherein said imaging data are low resolution imaging data while said reference imaging data are high resolution imaging data.

Preferably, the method of the first aspect of the invention comprises determining said thickness-density relationship previously to said step of providing measured variations of said imaging parameter.

For an embodiment, said thickness and density measurements include thickness and density measurements made on thin cortex regions of said reference cortical bone tissue structure. Preferably, said thin cortex regions of the reference cortical bone tissue structure have thicknesses below 3 mm.

For an embodiment, the region of bone tissue represented by said at least one representation defined by said imaging data includes, regarding cortical bone tissue, only thin cortex regions. Preferably, said thin cortex regions of the imaging data have thicknesses below 3 mm.

In other words, for the above mentioned embodiment, the imaging data including the cortical bone tissue structure of interest does not include data referring to thick cortical bone regions but only to thin cortical bone regions. The above cited prior art method [11] cannot be used to measure the cortical thickness and density with such imaging data, as the method requires regions of thick cortex to be present in the imaging data. In contrast, accurate cortical thickness and density measurements can be obtained by means of the method of the first aspect of the invention.

For an embodiment, the method of the first aspect of the invention comprises performing the above described steps for variations of the imaging parameter along a plurality of lines crossing the cortical bone tissue structure of interest through different portions thereof, preferably in substantially normal directions to respective cross-sections thereof.

Preferably, said measured variations determining said thickness-density relationship are obtained from multiple thickness and density measurements made on several reference cortical bone tissue structures of a plurality of subjects, none of which being said patient, and/or on several portions of each reference cortical bone tissue structure and/or on several reference cortical bone tissues structures of each of said subjects.

For an embodiment, said multiple thickness and density measurements are performed from measured variations of an imaging parameter of said reference imaging data, the latter defining at least one representation of a region of bone tissue of said subject and including a reference cortical bone tissue structure, said variations being measured along at least one line crossing said reference cortical bone tissue structure (preferably in a substantially normal direction to a cross-section thereof).

Said reference cortical bone tissue structure can be the same type as the cortical bone tissue structure of interest or a different type. In other words, if the cortical bone tissue structure of interest is, for example, a femoral cortex, the reference cortical bone tissue structure can be a femoral cortex or a cortex of a different bone, such as a vertebral cortex.

For a preferred embodiment, said subject or subjects is/are cadaveric specimen/specimens, such that a higher dose of radiation (in comparison with the level of radiation which can be applied to a living human being) can be applied thereto in order to perform said multiple thickness and density measurements, including those made on thin cortex regions, with a high accuracy.

The method further comprises, according to an embodiment, generating said measured variations of an imaging parameter of imaging data defining at least one representation of a region of bone tissue of a patient including said cortical bone tissue structure of interest, by means of the following steps:

receiving said imaging data defining at least one representation of a region of bone tissue of a patient including said cortical bone tissue structure of interest;

defining a line crossing said cortical bone tissue structure of interest; and measuring the variations of said imaging data along said line crossing said cortical bone tissue structure of interest.

The above mentioned function has, for an embodiment, second and third density parameters defining density along said line outside said cortical bone tissue structure of interest respectively to either side of said cortical bone tissue structure of interest, and also a position parameter defining the position of said cortical bone tissue structure of interest along the line, wherein said fitting also comprises searching for optimal values for said second and third density parameters and for said position parameter.

As stated above, the above cited imaging data, i.e. the ones obtained from the patient, are low resolution imaging data, i.e. clinical resolution imaging data, while the reference imaging data, i.e. the ones obtained from the subject which is not the patient, are high resolution imaging data, i.e. having a higher resolution than said imaging data obtained from the patient. Low resolution imaging data should have a pixel size of $0.3 \times 0.3$ mm$^2$ or higher, while high resolution imaging data should have a pixel size of $0.1 \times 0.1$ mm$^2$ or lower.

According to different embodiments, said reference imaging data are obtained using micro computed tomography and/or histological measurements, and said imaging data are obtained using computed tomography, magnetic resonance or three-dimensional reconstruction or three-dimensional modelling techniques using X-ray projective views.

According to an embodiment, each of said imaging data and said reference imaging data defines at least one three-dimensional representation of, respectively, a region of bone tissue of a patient including said cortical bone tissue structure of interest and a region of bone tissue of said subject and which includes said reference cortical bone tissue structure.

The method of the first aspect of the invention comprises, for an embodiment, determining said thickness-density relationship by computing a statistically representative profile over a cloud of points formed by said multiple thickness and density measurements.

Said statistically representative profile is, for variants of said embodiment, one of an average profile and a median profile.

Depending on the embodiment, said statistically representative profile provides one or more density values or a range of values for each thickness value, or provides one or more thickness values or a range of values for each density value.

A second aspect of the invention relates to a system for determining data defining an estimate of the thickness and density of a cortical bone tissue structure of interest from imaging data, the system comprising computing means including memory means and processing means, and being configured, arranged and adapted to implement the method of the first aspect of the invention.

The system of the second aspect of the invention further comprises, for an embodiment, display means connected to said computing means and adapted for displaying density and/or thickness maps on 2D or 3D representations of the cortical bone tissue structure of interest.

A third aspect of the invention relates to a computer program which includes program code instructions that when executed in a computer implement the steps of the method of the first aspect of the invention.

BRIEF DESCRIPTION OF THE FIGURES

The previous and other advantages and features will be more fully understood from the following detailed description of embodiments, with reference to the attached drawings, which must be considered in an illustrative and non-limiting manner, in which.

DETAILED DESCRIPTION

In the present section, a preferred implementation of the method of the first aspect of the invention is described, particularly in the form of a model-based approach for measuring the cortical bone thickness and density from clinical images. High resolution micro-CT data of proximal femurs were analysed to derive a relationship between cortical thickness and density. This thickness-density relationship was used as a prior information to obtain accurate measurements of cortical thickness and density from clinical CT volumes. The method was validated by comparing cortical thickness and density measurements estimated from simulated low resolution clinical CT volumes with direct measurements from micro-CT data.

Method:

A. Modelling Density Variations Across the Cortex

Figure 1:
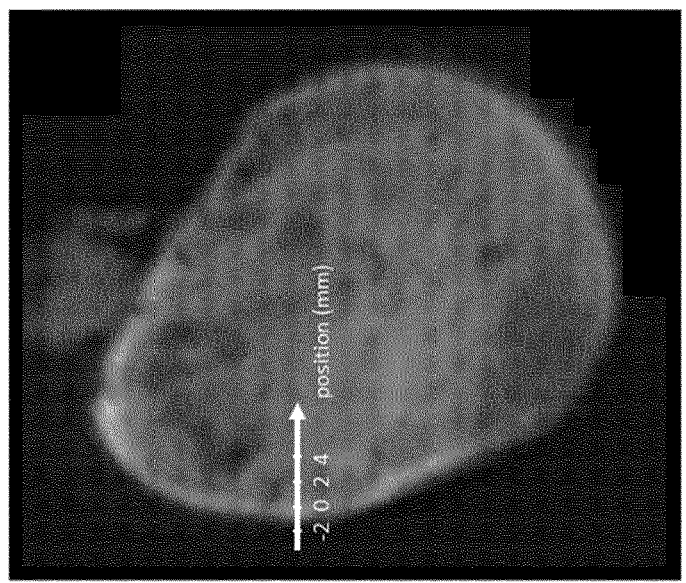
FIG. 1: Measuring density variations across the cortex in a proximal femur CT slice (left). The parameters y0, y1, y2 (density values in surrounding tissue, within the cortex, and within the trabecular bone respectively), t (cortical thickness), x1 (location of the center of the cortex) and σ (imaging blur) are optimized according to the method of the first aspect of the invention, so that the modelled density $y_{mod}$ matches the measured one $y_{mes}$ (right).
Figure 1:
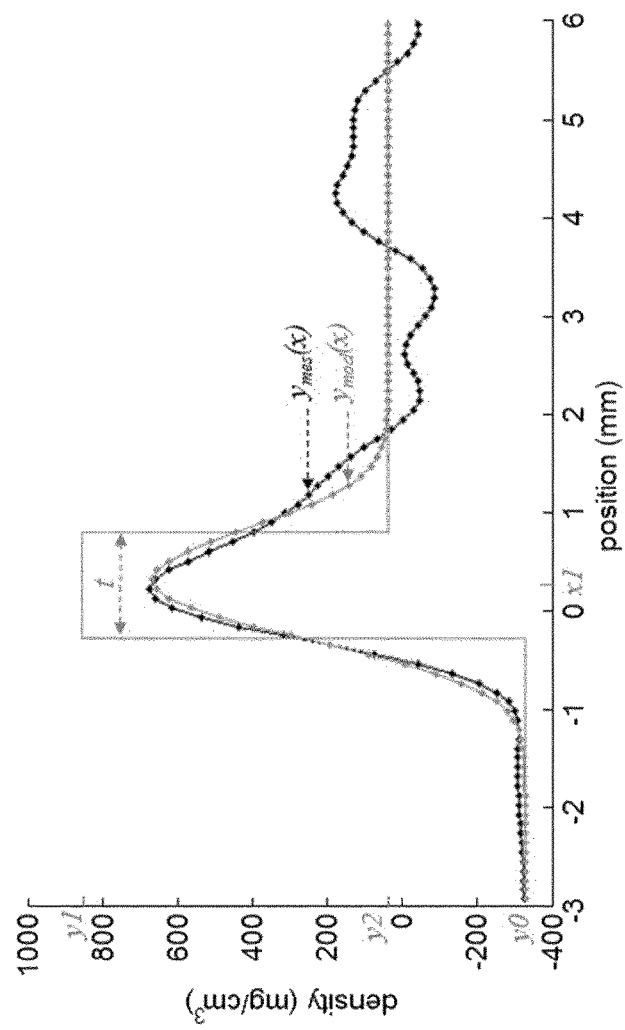

Given a CT volume of a bony structure, CT values can be sampled along a line crossing the cortex to measure the density variations $y_{mes}$. Similar to previous work [8, 10, 11], the variations of density across the cortex can be modelled as:

$$y_{mod}(x) = y0 + \frac{y1 - y0}{2}\left(1 + erf\left(\frac{x - \left(x1 - \frac{t}{2}\right)}{\sigma\sqrt{2}}\right)\right) + \frac{y2 - y1}{2}\left(1 + erf\left(\frac{x - \left(x1 + \frac{t}{2}\right)}{\sigma\sqrt{2}}\right)\right) \quad (1)$$

where x is the position across the cortex, y0, y1 and y2 are density values in surrounding tissue, within the cortex, and within the trabecular bone respectively, t is the cortical thickness, x1 is the location of the center of the cortex, and σ is the standard deviation of the assumed Gaussian imaging blur. The parameters of equation (1) should be optimized so that the modelled density $y_{mod}$ matches measured density data $y_{mes}$ (FIG. 1).

For clarity sake, it must be stated that $y_{mod}$ corresponds to, for the present embodiment, the previously called function, claimed and described in a previous section, to be fitted to the measured variations of the imaging parameter, i.e. to $y_{mes}$, and y1, y0 and y2 correspond to, respectively, the parameters of the function called in the previous section as first, second and third density parameters, while σ corresponds to the previously called parameter representing the blur of the imaging data, and x1 to the previously called position parameter, the optimal values of all of said parameters being searched during the fitting of $y_{mod}$ to $y_{mes}$.

B. Prior Information about the Thickness-Density Relationship

In the case of clinical CT data, the method of the present invention solves equation (1) by incorporating prior information about the relationship between the cortical thickness t and the cortical density y1, such as:

$$y1 = f(t) \quad (2)$$

Alternatively to (2), the thickness-density relationship can be express as t=f(y1).

Figure 2:
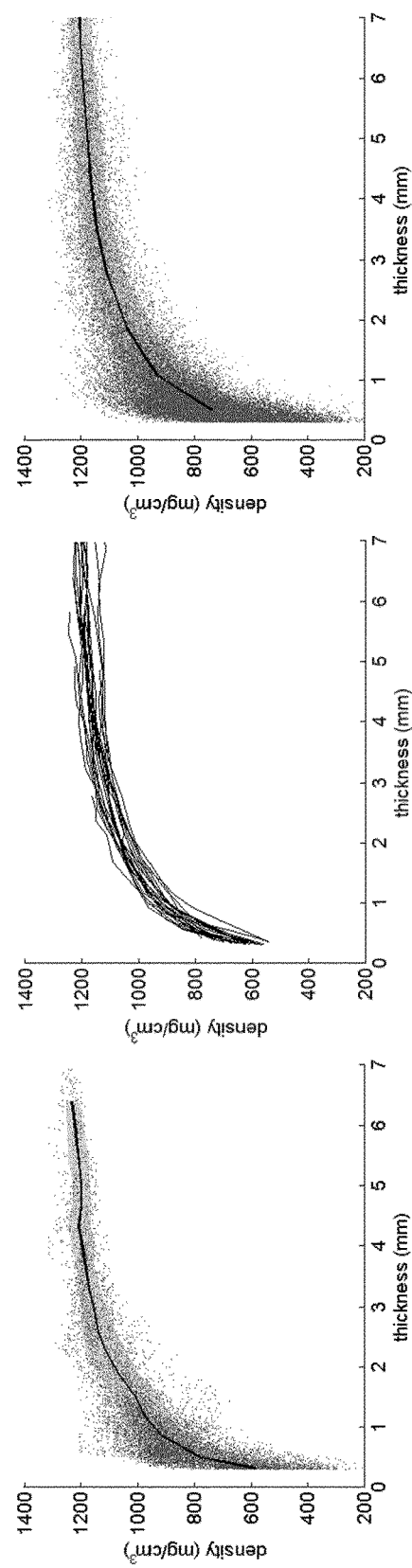
FIG. 2 shows three diagrams built from multiple thickness and density measurements for one specimen (left) and 23 specimens (middle and right), to determine the thickness-density relationship according to the method of the first aspect of the present invention. Specifically, said diagrams refer to cortical density against thickness, average profile and standard deviation for one specimen (left), superimposition of the density profiles computed from 23 specimens (middle) and cortical density against thickness, average profile and standard deviation for the 23 specimens (right).

Thickness-density relationship was investigated using a database of micro-CT scans of cadaver proximal femurs. A database of 23 samples obtained from 8 female and 15 male donors, with a mean age of 75.0±9.1 years [61 years-93 years] was used. 13 were left femurs and 10 right femurs. Micro-CT scans (XtremeCT, Scanco Medical AG, Brüttisellen, Switzerland) were performed with a voxel size of 0.082×0.082×0.082 mm³. Images were calibrated according to the protocol recommended by the manufacturer in order to recover bone density values at each voxel. A threshold was applied to each micro CT volume, and a 3D closing followed by a filling operation were performed to create a mask and a surface mesh over the proximal femur. At each node of the surface mesh, the normal vector to the surface was computed and 100 points were sampled along the normal. The density profile was computed by interpolating in the micro CT volume at each sampled points. The model-based FWHM approach was used to obtain an estimate of the cortical thickness and density each node of the surface mesh. The model proposed in Equation (1) was fitted to the measured density profile using the Levenberg-Marquardt algorithm [12] and fixing y1 at the maximum value observed in the density profile. The optimal value for cortical thickness and the value used for y1 were stored. Cortical thickness and density solutions found at each node of the surface mesh can be plotted and the average profile computed (FIG. 2, left). By applying the same process to every specimens, 23 average profiles can be computed and superimposed in the same graph (FIG. 2, middle). Finally, cortical thickness and density solutions computed for the 23 specimens were gathered and the average profile for the whole dataset computed (FIG. 2, right). This average profile computed from the 23 specimens was stored as a look-up table, and will determine the thickness-density relationship of Equation (2).

C. Computing Cortical Thickness and Density from Clinical CT Data

Given a clinical CT volume of a bony structure, the system composed by Equations (1) and (2) is solved using the Levenberg-Marquardt algorithm to fit the modelled density profile $y_{mod}$ to the measured data $y_{mes}$ (FIG. 1). The parameters y0, y1, y2, t and x1 are optimized, while at each iteration of the optimization process the cortical density y1 is estimated using the current instance for the cortical thickness t and the thickness-density look-up table.

D. Method Evaluation

The ability of the method to provide an accurate estimation of the cortical thickness and density from clinical CT data was evaluated. Low resolution CT volumes were generated from the 23 micro CT-scans of cadaveric proximal femur specimens. A bicubic interpolation was performed in the original micro CT-scans volumes (voxel size: 0.082×0.082×0.082 mm³) to generate volumes with the following voxel sizes: 0.33×0.33×1.0 mm³, 0.66×0.66×2.0 mm³ and 1.0×1.0×3.0 mm³, the first two dimensions corresponding to the transverse plane. The accuracy of the cortical thickness and density calculation method was evaluated using a leave-one-out cross validation. A sample ($i^{th}$ specimen) was chosen among the 23 specimens. The previously described model-based FWHM approach and the micro-CT high resolution volume of the $i^{th}$ specimen was used to measure the cortical thickness and density at each node of the femoral shape. Using the remaining 22 micro-CT samples, a density-thickness relationship was determined following the pipeline described above (section B). This density-thickness relationship was used as a prior information for the method of the present invention (section C) to estimate the cortical thickness and density from the low resolution clinical CT volumes generated for the $i^{th}$ specimen. Cortical thickness and density estimated from the low resolution clinical CT volumes were compared with those computed using the high resolution micro-CT volume, and the process was repeated for the 23 samples in order to evaluate the accuracy of the method over the whole dataset.

Figure 3:
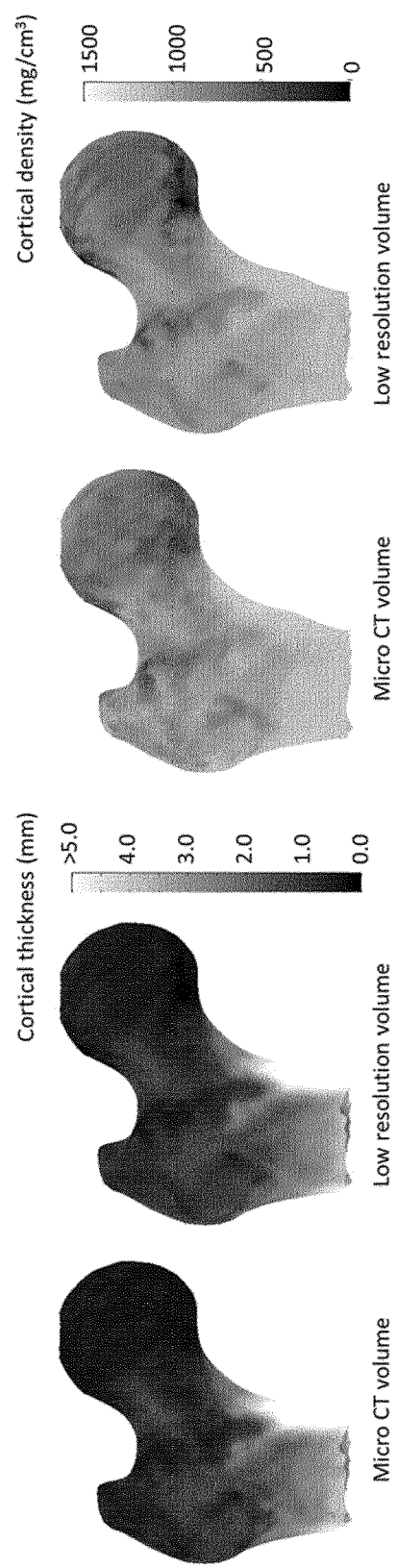
FIG. 3: Colour maps over the femoral shape showing the cortical thickness (left) and density (right) computed using high resolution micro CT and low resolution volumes for one sample.

Results:

A comparison between the cortical thickness and density computed using high resolution micro CT (FWHM approach) and low resolution clinical CT volumes is proposed for one sample in FIG. 3.

The mean (±standard deviation) accuracy computed over the 23 samples was 0.08±0.21 mm for the cortical thickness and −12±93 mg/cm³ for the density, when computed for cortices in the range [0.3 mm, 6.0 mm] and using the clinical CT volumes with the highest resolution (voxel size of 0.33×0.33×1.0 mm³). Using the lowest resolution volumes (voxel size of 1.0×1.0×3.0 mm³), the accuracy was 0.10±0.25 mm and −11±121 mg/cm³. Detailed results for cortices in the range [0.3 mm, 1.0 mm[, [1.0 mm, 3.0 mm[ and [3.0 mm, 6.0 mm] are provided in Table 1. Thickness estimation errors were higher when computed for thick cortex ([3.0 mm, 6.0 mm] range: standard deviation between 0.32 mm and 0.35 mm) than for thin cortex (standard deviation between 0.16 mm and 0.21 mm). The opposite was observed for the density, with lower estimation errors when computed for thick cortex in comparison with thin cortex. As would be expected, a trend for the method accuracy to decrease with image resolution was observed, for both cortical thickness and density.

TABLE 1

Cortical thickness and density estimation accuracy (Mean ± Standard deviation) for the 23 samples, and comparison with results provided by Treece et al. [11]

| Voxel size (mm³) | Cortical thickness (mm) Thickness range (mm) | | | | Density (mg/cm³) Thickness range (mm) | | | |
| --- | --- | --- | --- | --- | --- | --- | --- | --- |
| | [3.0, 6.0] | [1.0, 3.0[ | [0.3, 1.0[ | [0.3, 6.0] | [3.0, 6.0] | [1.0, 3.0[ | [0.3, 1.0[ | [0.3, 6.0] |
| 0.33 × 0.33 × 1.0 | −0.04 ± 0.32 | 0.04 ± 0.24 | 0.12 ± 0.16 | 0.08 ± 0.21 | −4 ± 47 | −5 ± 76 | −16 ± 104 | −12 ± 93 |
| 0.66 × 0.66 × 2.0 | −0.06 ± 0.33 | 0.06 ± 0.26 | 0.14 ± 0.18 | 0.10 ± 0.23 | −4 ± 47 | −2 ± 77 | −9 ± 116 | −7 ± 102 |
| 1.0 × 1.0 × 3.0 | −0.08 ± 0.35 | 0.07 ± 0.28 | 0.14 ± 0.21 | 0.10 ± 0.25 | −4 ± 47 | −1 ± 78 | −16 ± 140 | −11 ± 121 |
| Treece et al. [11] 'CBM v3' method | | | | | | | | |
| 0.33 × 0.33 × 1.0 | 0.04 ± 0.25 | 0.26 ± 0.40 | 0.04 ± 0.31 | — | 27 ± 109 | −89 ± 160 | −30 ± 264 | — |

Figure 4:
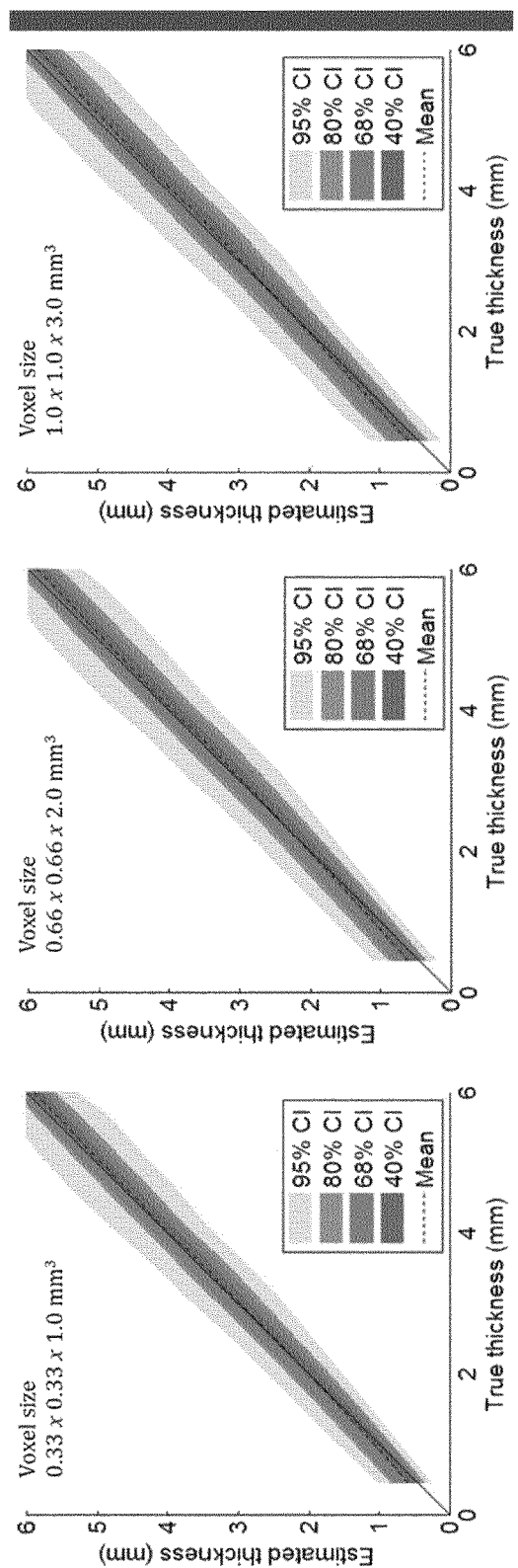
FIG. 4: Thickness estimated from the three set of clinical CT volumes (mean and confidence intervals (CI)), using the method of the first aspect of the invention, against true thickness, for the 23 samples.
Figure 5:
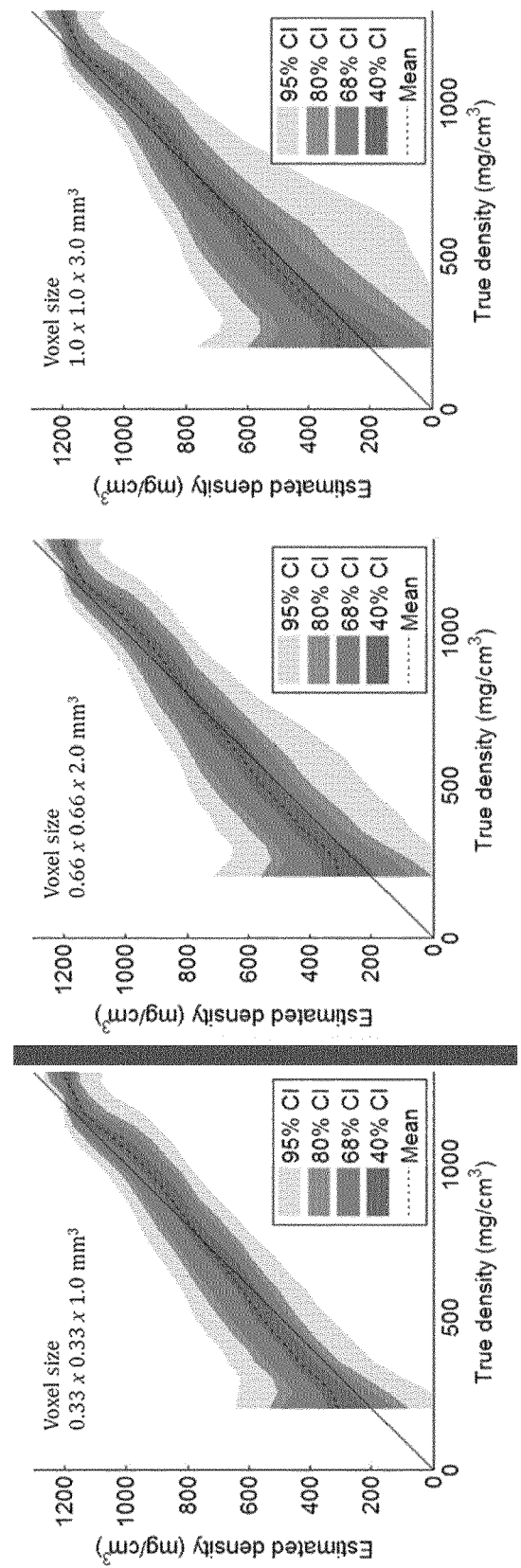
FIG. 5: Density estimated from the three set of clinical CT volumes (mean and confidence intervals), using the method of the first aspect of the invention, against true density for the 23 samples.
Figure 6:
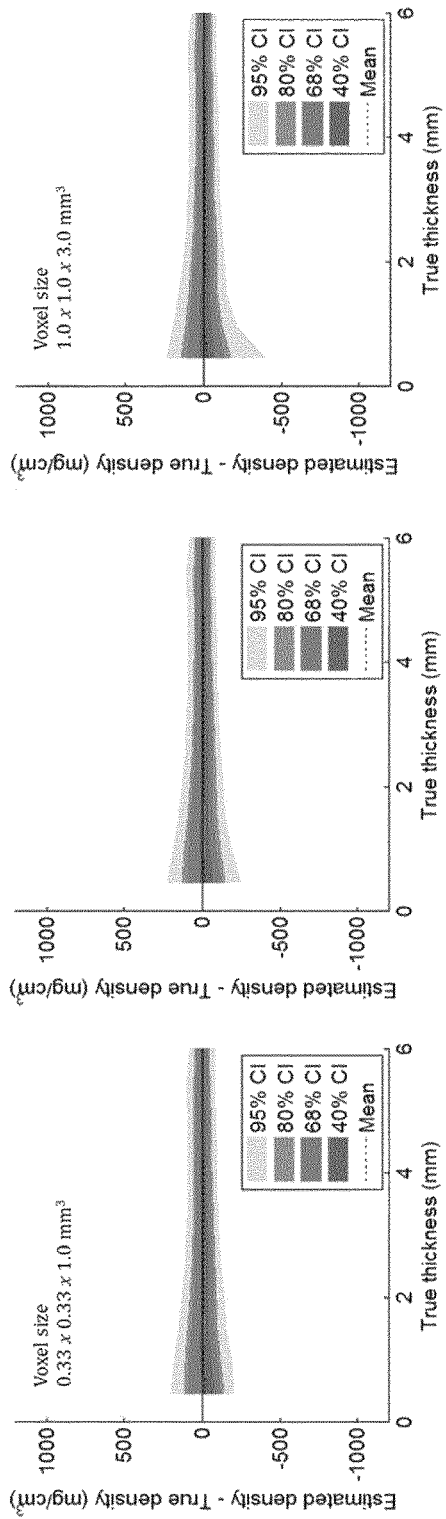
FIG. 6: Differences between density estimated from the three set of clinical CT volumes and true density (mean and confidence intervals), using the method of the first aspect of the invention, against true thickness for the 23 samples.

In FIG. 4 the cortical thickness estimated from the low resolution clinical CT volumes is plotted against the thickness calculated from micro CT volumes ('true thickness') for the 23 samples. The mean values together with the 40%, 68% (equivalent to a one-standard-deviation range), 80% and 95% confidence intervals are shown. A similar plot is provided for the cortical density (FIG. 5). In FIG. 6 are plotted the cortical density errors (estimated density−true density) against the true thickness.

As stated above, the proposed cortical thickness and density calculation method was evaluated using simulated clinical CT data with voxel sizes of 0.33×0.33×1.0 mm³, 0.66×0.66×2.0 mm³ and 1.0×1.0×3.0 mm³, representing typical settings for clinical routine CT scanning. In spite of a pixel dimension three times lower, the results obtained using the volumes with the lowest resolution were rather close to those obtained with the highest resolution images (thickness: 0.25 mm against 0.21 mm for the standard deviation and density: 93 mg/cm³ against 121 mg/cm³, Table 1). The bias was also rather low for all the tested configurations (between 0.08 mm and 0.10 mm for the cortical thickness, and between −7 and −12 mg/cm³ for the density, when observed for cortices in the range [0.3, 6.0]).

In previous work from Treece et al. [11] several methods for cortical thickness and density estimation were evaluated and compared, including the FWHM method [6], the 'preset blur' method, which rely on a prior estimate of the blur, the 'nothing preset' approach as proposed by Pakdel et al. [7] the 'CBM v1' method as proposed by Treece et al. [10] and the new 'CBM v2' and 'CBM v3' methods introduced in Treece et al. [11] The evaluation was performed using 70 femur specimens. Cortical thickness and density estimated from clinical CT volumes (voxel size: 0.33×0.33×1.0 mm³) were compared with calculation from micro CT volumes (voxel size: 0.082×0.082×0.082 mm³). The 'CBM v3' method was found to provide the best results in estimating the cortical thickness and density from clinical CT data. A comparison of the method of the present invention with results obtained by Treece et al. using the 'CBM v3' method [11] is proposed in Table 1. Although the samples included in both studies were different, this comparison shows that the current method provides an estimation of the cortical thickness with a similar accuracy in comparison with the 'CBM v3' method. With regards to the density estimation, the current implementation showed lower bias and errors (standard deviation) than the 'CBM v3' method (Table 1).

Figure 7:
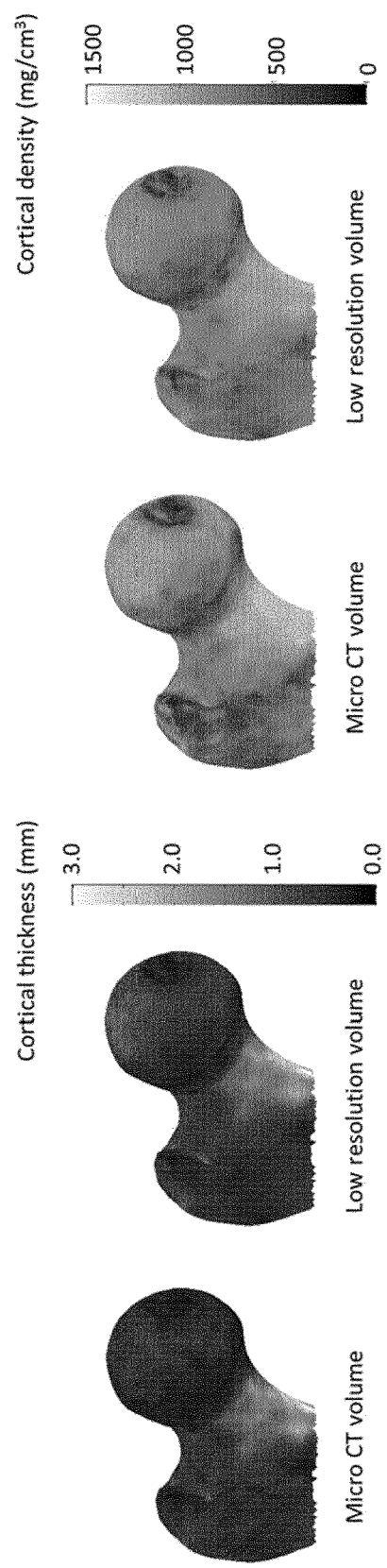
FIG. 7: Colour maps over the femoral shape showing the cortical thickness (left) and density (right) computed using high resolution micro CT and low resolution volumes for one sample. Maximum value for cortical thickness computed from the micro CT volume was 2.97 mm.

As previously mentioned, state-of-the-art algorithms for cortical thickness and/or density estimation [9-11, 13] require the analysis of regions of thick cortex (typically cortex above 3 mm) in the CT data. If no region of thick cortex is present in the image, such algorithms cannot be used in a straightforward manner to provide an estimation of the cortical thickness and/or density. One of the advantages of the method of the present invention is that the cortical thickness and density can be computed even if no region of thick cortex is present in the image. FIG. 7 shows a comparison between cortical thickness and density computed using high resolution micro CT and low resolution volumes for one femur sample. The analysis was limited to the upper part of the proximal femur, where the maximal value for cortical thickness was 2.97 mm. This figure shows that, contrary to the methods of the state of the art, even in the absence of region of thick cortex, the method of the first aspect of the present invention is able to provide an accurate estimation of the cortical thickness and density.

Using a thickness-density relationship build from reference imaging data to constrain the model of Equation (1) is not a trivial solution and, prior to this study, there was no evidence that implementing such a solution would provide accurate estimates of the cortical thickness and density. First, the existence of a relationship between thickness and density has to be demonstrated. This has been investigated in the current study by using high resolution images of a dataset of cadaver proximal femur. To the best of our knowledge, this is the first time that cortical thickness and density measurements obtained using high resolution imaging techniques and cadaver specimens are analysed to study those aspects. FIG. 2 shows that very similar thickness-density relationships are observed for all the cadaver proximal femur included in this study, which led us to investigate about the feasibility of using an average thickness-density relationship in Equation (1). In a second step, the ability of the approach to provide accurate estimates of the cortical thickness and density using low resolution images was investigated, and Table 2 shows that the current approach provides a similar of better accuracy than state of the art approaches [11].

To conclude, the method of the present invention provides a new model-based approach for measuring the cortical bone thickness and density from clinical low resolution images, incorporating a prior thickness-density relationship computed using high resolution micro-CT data. This method opens the way for the quantification of cortical bone thickness and density using clinical routine techniques such as CT, QCT, MRI, or 3D reconstruction or modelling methods from 2D projective images.

A person skilled in the art could introduce changes and modifications in the embodiments described without departing from the scope of the invention as it is defined in the attached claims.

REFERENCES

1. O. Johnell and J. A. Kanis, "*An estimate of the worldwide prevalence and disability associated with osteoporotic fractures*". Osteoporos Int 17, 1726-1733 (2006).
2. A. El Maghraoui and C. Roux, "*DXA scanning in clinical practice*". QJM 101, 605-617 (2008).
3. V. Bousson, A. Le Bras, F. Roqueplan, Y. Kang, D. Mitton, S. Kolta, C. Bergot, W. Skalli, E. Vicaut, W. Kalender, K. Engelke and J. D. Laredo, "*Volumetric quantitative computed tomography of the proximal femur: relationships linking geometric and densitometric variables to bone strength. Role for compact bone*". Osteoporos Int 17, 855-864 (2006).
4. L. Humbert, T. Whitmarsh, L. M. Del Rio Barquero, M. De Craene and A. F. Frangi, ES2382774.
5. T. Whitmarsh, L. Humbert, M. De Craene, L. Del Rio Barquero and A. Frangi, "*Reconstructing the 3D Shape and Bone Mineral Density Distribution of the Proximal Femur from Dual-energy X-ray Absorptiometry*". IEEE Trans Med Imaging (2011).
6. S. Prevrhal, K. Engelke and W. A. Kalender, "*Accuracy limits for the determination of cortical width and density: the influence of object size and CT imaging parameters*". Physics in medicine and biology 44, 751-764 (1999).
7. A. Pakdel, N. Robert, J. Fialkov, A. Maloul and C. Whyne, "*Generalized method for computation of true thickness and x-ray intensity information in highly blurred sub-millimeter bone features in clinical CT images*" Physics in medicine and biology 57, 8099-8116 (2012).
8. G. J. Streekstra, S. D. Strackee, M. Maas, R. ter Wee and H. W. Venema, "*Model-based cartilage thickness measurement in the submillimeter range*". Medical physics 34, 3562-3570 (2007).
9. G. M. Treece, A. H. Gee, P. M. Mayhew and K. E. Poole, "*High resolution cortical bone thickness measurement from clinical CT data*". Med Image Anal 14, 276-290 (2010).
10. G. M. Treece, K. E. Poole and A. H. Gee, "*Imaging the femoral cortex: thickness, density and mass from clinical CT*". Med Image Anal 16, 952-965 (2012).
11. G. M. Treece and A. H. Gee, "*Independent measurement of femoral cortical thickness and cortical bone density using clinical CT*". Med Image Anal 20, 249-264 (2015).
12. J. Moré, "*The Levenberg-Marquardt algorithm: Implementation and theory*", in Numerical Analysis, Vol. 630, edited by G. A. Watson (Springer Berlin Heidelberg, 1978), pp. 105-116.
13. G. M. Treece and K. E. Poole, WO2011042738.

The invention claimed is:

1. A computer-implemented method for determining data defining an estimate of the thickness and density of a cortical bone tissue structure of interest from imaging data, the method comprising:
   providing measured variations of an imaging parameter of imaging data defining at least one representation of a region of bone tissue of a patient including said cortical bone tissue structure of interest, said variations being measured along a line crossing said cortical bone tissue structure of interest and being representative of variations of bone tissue structure density, wherein said imaging data is low resolution imaging data;
   modelling said variations of said imaging parameter along said line as a function having at least one parameter defining said thickness of said cortical bone tissue structure of interest along said line, at least a first density parameter defining said density of said cortical bone tissue structure of interest along said line and at least one parameter representing the blur of said imaging data;
   determining a thickness-density relationship between cortical bone tissue structure density and cortical bone tissue structure thickness, wherein said thickness-density relationship is determined from multiple thickness and density measurements made on reference imaging data of a reference cortical bone tissue structure of a subject which is not said patient, wherein said reference imaging data is high resolution imaging data; and
   fitting said function to said measured variations of said imaging parameter;
   wherein said fitting comprises searching for optimal values for said at least one parameter representing the blur of said imaging data, for said at least one parameter defining said thickness of said cortical bone tissue structure of interest, and for said at least first density parameter defining said density of said cortical bone tissue structure of interest, while ensuring said at least first density parameter and said at least one parameter defining said thickness to substantially follow said thickness-density relationship; and further wherein said optimal values for said at least one parameter defining said thickness of said cortical bone tissue structure of interest and for said at least first density parameter comprise, respectively, data defining said estimate of said thickness and data defining said estimate of said density of the cortical bone tissue structure of interest.

2. The computer-implemented method of claim 1, wherein said low resolution imaging data has a pixel size of 0.3×0.3 mm² or higher, while said high resolution imaging data has a pixel size of 0.1×0.1 mm² or lower.

3. The computer-implemented method of claim 1, wherein said reference imaging data are obtained using micro computed tomography and/or histological measurements, and said imaging data are obtained using computed tomography, magnetic resonance or three-dimensional reconstruction or three-dimensional modelling techniques using X-ray projective views.

4. The computer-implemented method of claim 1, comprising determining said thickness-density relationship previously to said step of providing measured variations of said imaging parameter.

5. The computer-implemented method of claim 1, wherein said multiple thickness and density measurements include thickness and density measurements made on thin cortex regions of said reference cortical bone tissue structure.

6. The computer-implemented method of claim 1, wherein the region of bone tissue represented by said at least one representation defined by said imaging data includes, regarding cortical bone tissue, only thin cortex regions.

7. The computer-implemented method of claim 5, wherein said thin cortex regions have thicknesses below 3 mm.

8. The computer-implemented method of claim 1, wherein said multiple thickness and density measurements are performed from measured variations of an imaging parameter of said reference imaging data, the reference imaging data defining at least one representation of a region of bone tissue of said subject and including a reference cortical bone tissue structure, said variations being measured along at least one line crossing said reference cortical bone tissue structure.

9. The computer-implemented method of claim 1, further comprising generating said measured variations of an imaging parameter of imaging data defining at least one representation of a region of bone tissue of a patient including said cortical bone tissue structure of interest by:
receiving said imaging data defining at least one representation of a region of bone tissue of a patient including said cortical bone tissue structure of interest;
defining a line crossing said cortical bone tissue structure of interest; and
measuring the variations of said imaging data along said line crossing said cortical bone tissue structure of interest.

10. The computer-implemented method of claim 1, wherein said function has second and third density parameters defining density along said line outside said cortical bone tissue structure of interest respectively to either side of said cortical bone tissue structure of interest, and also a position parameter defining the position of said cortical bone tissue structure of interest along said line, wherein said fitting also comprises searching for optimal values for said second and third density parameters and for said position parameter.

11. The computer-implemented method of claim 1, wherein each of said imaging data and said reference imaging data defines at least one three-dimensional representation of, respectively, a region of bone tissue of a patient including said cortical bone tissue structure of interest and a region of bone tissue of said subject and which includes said reference cortical bone tissue structure.

12. The computer-implemented method of claim 1, wherein said measured variations determining said thickness-density relationship are obtained from multiple thickness and density measurements made on at least one of:
several reference cortical bone tissue structures of a plurality of subjects, none of which being said patient;
several portions of each reference cortical bone tissue structure; and
several reference cortical bone tissues structures of each of said subjects.

13. The computer-implemented method of claim 1, wherein said subject is a cadaveric specimen.

14. The computer-implemented method of claim 1, comprising determining said thickness-density relationship by computing a statistically representative profile over a cloud of points formed by said multiple thickness and density measurements.

15. The computer-implemented method of claim 14, wherein said statistically representative profile is one of an average profile and a median profile.

16. The computer-implemented method of claim 15, wherein said statistically representative profile provides one or more density values or a range of values for each thickness value, or provides one or more thickness values or a range of values for each density value.

17. A system for determining data defining an estimate of the thickness and density of a cortical bone tissue structure of interest from imaging data, the system comprising one or more computers including memory and processors, and being configured to implement a method for determining data defining an estimate of the thickness and density of a cortical bone tissue structure of interest from imaging data, the method comprising:
providing measured variations of an imaging parameter of imaging data defining at least one representation of a region of bone tissue of a patient including said cortical bone tissue structure of interest, said variations being measured along a line crossing said cortical bone tissue structure of interest and being representative of variations of bone tissue structure density, wherein said imaging data are low resolution imaging data;
modelling said variations of said imaging parameter along said line as a function having at least one parameter defining said thickness of said cortical bone tissue structure of interest along said line, at least a first density parameter defining said density of said cortical bone tissue structure of interest along said line and at least one parameter representing the blur of said imaging data;
determining a thickness-density relationship between cortical bone tissue structure density and cortical bone tissue structure thickness, wherein said thickness-density relationship is determined from multiple thickness and density measurements made on reference imaging data of a reference cortical bone tissue structure of a subject which is not said patient, wherein said reference imaging data are high resolution imaging data; and
fitting said function to said measured variations of said imaging parameter;
wherein said fitting comprises searching for optimal values for said at least one parameter representing the blur of said imaging data, for said at least one parameter defining said thickness of said cortical bone tissue structure of interest and for said at least first density parameter defining said density of said cortical bone tissue structure of interest, while ensuring said at least first density parameter and said at least one parameter defining said thickness to substantially follow said thickness-density relationship; and further wherein said optimal values for said at least one parameter defining said thickness of said cortical bone tissue structure of interest and for said at least first density parameter comprise, respectively, data defining said estimate of said thickness and data defining said estimate of said density of the cortical bone tissue structure of interest.

18. A non-transitory computer program product, which includes program code instructions stored on at least one computer readable medium which, when executed in a computer, implement the steps of a method for determining data defining an estimate of the thickness and density of a cortical bone tissue structure of interest from imaging data, the method comprising:
providing measured variations of an imaging parameter of imaging data defining at least one representation of a region of bone tissue of a patient including said cortical bone tissue structure of interest, said variations being measured along a line crossing said cortical bone tissue structure of interest and being representative of variations of bone tissue structure density, wherein said imaging data are low resolution imaging data;
modelling said variations of said imaging parameter along said line as a function having at least one parameter defining said thickness of said cortical bone tissue structure of interest along said line, at least a first density parameter defining said density of said cortical bone tissue structure of interest along said line and at least one parameter representing the blur of said imaging data;
determining a thickness-density relationship between cortical bone tissue structure density and cortical bone tissue structure thickness, wherein said thickness-density relationship is determined from multiple thickness and density measurements made on reference imaging data of a reference cortical bone tissue structure of a subject which is not said patient, wherein said reference imaging data are high resolution imaging data; and fitting said function to said measured variations of said imaging parameter;

wherein said fitting comprises searching for optimal values for said at least one parameter representing the blur of said imaging data, for said at least one parameter defining said thickness of said cortical bone tissue structure of interest and for said at least first density parameter defining said density of said cortical bone tissue structure of interest, while ensuring said at least first density parameter and said at least one parameter defining said thickness to substantially follow said thickness-density relationship; and further wherein said optimal values for said at least one parameter defining said thickness of said cortical bone tissue structure of interest and for said at least first density parameter comprise, respectively, data defining said estimate of said thickness and data defining said estimate of said density of the cortical bone tissue structure of interest.

19. The computer-implemented method of claim 12, wherein said subjects are cadaveric specimens.

* * * * *